(12) United States Patent
Chen et al.

(10) Patent No.: US 7,930,033 B2
(45) Date of Patent: Apr. 19, 2011

(54) APPENDICULAR AND RECTAL STIMULATOR DEVICE FOR DIGESTIVE AND EATING DISORDERS

(76) Inventors: Jianfeng Chen, Tulsa, OK (US); Yong Lei, Edmond, OK (US)

( * ) Notice: Subject to any disclaimer, the term of this patent is extended or adjusted under 35 U.S.C. 154(b) by 447 days.

(21) Appl. No.: 11/893,786

(22) Filed: Aug. 17, 2007

(65) Prior Publication Data

US 2009/0048639 A1   Feb. 19, 2009

(51) Int. Cl.
*A61N 1/04* (2006.01)
(52) U.S. Cl. ......... 607/40; 607/1; 607/2; 607/3; 607/41; 607/100; 607/103; 607/113; 607/115; 607/116; 607/118; 607/133
(58) Field of Classification Search .................. 607/1–3, 607/40–41, 100, 103, 113, 115, 116, 118, 607/133
See application file for complete search history.

(56) References Cited

U.S. PATENT DOCUMENTS

| 5,170,800 | A | * | 12/1992 | Smith et al. .................. 600/564 |
| 5,690,691 | A | | 11/1997 | Chen et al. |
| 6,826,428 | B1 | | 11/2004 | Chen et al. |
| 7,054,690 | B2 | | 5/2006 | Imran |
| 7,118,531 | B2 | | 10/2006 | Krill et al. |
| 2002/0198470 | A1 | | 12/2002 | Imran et al. |
| 2003/0018367 | A1 | * | 1/2003 | DiLorenzo ...................... 607/46 |
| 2004/0088022 | A1 | | 5/2004 | Chen |
| 2005/0222637 | A1 | | 10/2005 | Chen |
| 2005/0222638 | A1 | | 10/2005 | Foley et al. |

OTHER PUBLICATIONS

Capsule Endoscopy; www.givenimaging.com/cultures/en-US/given/english.
Smartpill; www.smartpillcorp.com.
Zhang, J, J.D.Z. Chen; Systematic Review; Applications and Future of Gastric Electrical Stimulation; Alimentary Pharmacology & Therapeutics 2006; pp. 991-1002.
Shi Liu, M.D., et al., Therapeutic Potential of Duodenal Electrical Stimulation for Obesity: Acute Effects on Gastric Emptying and Water Intake; American Journal of Gastroenterology 2005; pp. 792-796.

* cited by examiner

*Primary Examiner* — Carl H Layno
*Assistant Examiner* — Deborah Malamud
(74) *Attorney, Agent, or Firm* — Dunlap Codding P.C.

(57) ABSTRACT

A method of using a stimulation device to emit a medium to an appendicular region and/or rectal region of a user for treatment of a gastrointestinal disorder is described. The method includes placing the stimulation device into the appendicular region and/or rectal region, and delivering the medium, wherein the medium stimulates at least a portion of the enteric nervous system. Additionally, apparatus and delivery devices are disclosed.

28 Claims, 3 Drawing Sheets

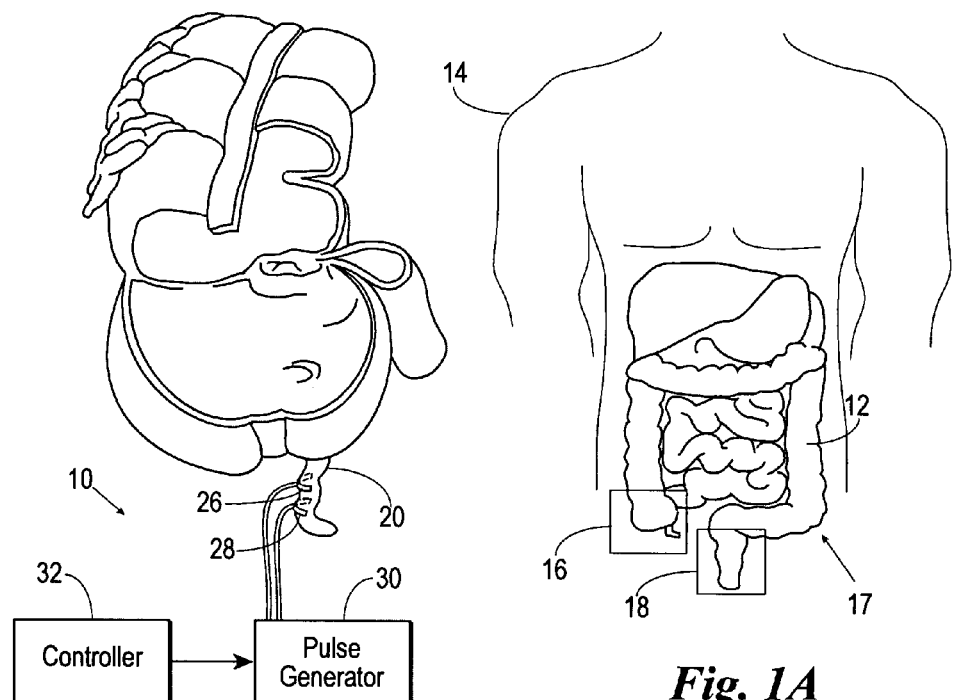
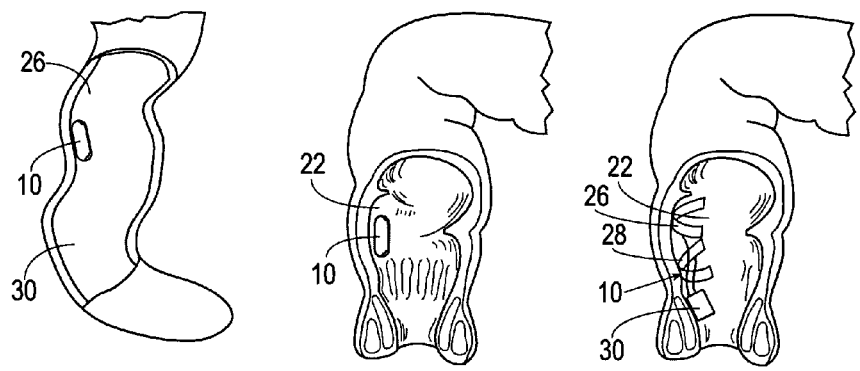

APPENDICULAR AND RECTAL STIMULATOR DEVICE FOR DIGESTIVE AND EATING DISORDERS

CROSS-REFERENCE TO RELATED APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO A "SEQUENCE LISTING", A TABLE, OR A COMPUTER PROGRAM LISTING APPENDIX SUBMITTED ON A COMPACT DISC AND AN INCORPORATION BY REFERENCE OF THE MATERIAL ON THE COMPACT DISC

Not applicable.

BACKGROUND OF THE INVENTION

Electrical stimulation, or pacing, was advocated as a possible treatment for gastric motor dysfunction as early as 1963. Experimentation in the late 1960s and early 1970s, began to demonstrate the significance of gastrointestinal myoelectrical activity and its relation to contractile activity.

Electrical stimulation has been shown to be able to alter, inhibit, or excite gastrointestinal motor functions, activate intrinsic and extrinsic neuronal pathways and/or solicit hormonal/peptide releases. Because of these characteristics, electrical stimulation has been shown to be effective in normalizing gastric dysrhythmia, accelerating gastric emptying, and reducing symptoms such as nausea and vomiting. Recently, electrical stimulation has also been studied as a therapy for obesity.

Obesity is a growing public health problem with a lack of satisfactory treatments. Recent research seems to suggest that electrical stimulation may delay gastric emptying and thereby assist in prolonging meal intervals and reducing frequent snacking without the risks and complications of surgery. Fluid intake may also be induced by electrical stimulation so as to assist in reducing appetite, for example, by reducing the capacity for accommodating food within the gastrointestinal tract as detailed in "Therapeutic Potential of Duodenal Electrical Stimulation for Obesity: Acute Effects on Gastric Emptying and Water Intake" by Shi Liu, Xiaohua Hou, and J. D. Z. Chen in *American Journal of Gastroenterology*, Volume 100, pages 792-796 (2005) that is hereby incorporated by reference in its entirety.

Most of the devices developed to provide for electrical stimulation are located within the gastric region of the gastrointestinal tract. See GASTROINTESTINAL PACEMAKER HAVING PHASED MULTIPOINT STIMULATION (U.S. Pat. No. 5,690,691), GASTROINTESTINAL ELECTRICAL STIMULATION (U.S. Pat. No. 6,826,428), SENSOR BASED GASTROINTESTINAL ELECTRICAL STIMULATION FOR THE TREATMENT OF OBESITY OR MOTILITY DISORDERS (U.S. Patent Publication No. 2005/0222638), PROCESS FOR ELECTROSTIMULATION TREATMENT OF MORBID OBESITY (U.S. Pat. Publication No. 2004/0088022), TACHYGASTRIAL ELECTRICAL STIMULATION (U.S. Pat. Publication No. 2005/0222637), each of which is hereby incorporated by reference in its entirety.

The enteric nervous system (ENS) contains numerous short axon and inter-neurons in the intestinal wall. The vast number of neurons and neuronal connections in the intestinal ENS carry out many digestive reflexes independent from the central nervous system. For example, the complex movements of peristalsis seen in the esophagus, stomach, and intestine are entirely initiated and regulated by the ENS. In addition, many neurotransmitters are released by ENS neurons to control glandular secretion and muscle contraction in the gut wall. Research has shown that stimulation in one area of the intestinal tract can provide stimulation in a whole other area within the ENS system.

BRIEF SUMMARY OF THE INVENTION

In one embodiment, the present invention is related to a method of using a stimulation device to emit a medium in the appendicular region for treatment of a gastrointestinal disorder. In general, a stimulation device is inserted into the luminal cavity of the appendix and delivers the medium for treatment of the gastrointestinal disorder or eating disorder. The stimulation device may be placed endoscopically and/or surgically inserted into the appendix. For example, the stimulation device may be inserted into the cavity of the appendix using endoscopic techniques by placing the stimulation device in a pouch underneath the skin.

In one version, the stimulation device comprises at least two electrodes sized and shaped for insertion into the mucosa or submucosa of the appendix. The electrodes are in communication with a pulse generator located in the luminal cavity of the appendix. In another version, a pair of stimulation electrodes are inserted into the seromuscular layer of the appendix and connected to a generator inserted subcutaneously within the abdominal region.

In general, the pulse generator delivers pulses to the electrodes located in the mucosa and/or submucosa or serosa of the appendix such that the electrodes provide stimulation to the appendicular wall and thus the gastrointestinal tract through the enteric nervous system of the user. The pulses can be provided in a variety of different manners, such as intermittent pulses, continuous pulses, and/or a train of intermittent and/or continuous pulses. Such pulses can be delivered via the pulse generator to the electrodes via any suitable medium, such as electricity, acoustic waves, radiation, photons, or the like.

The method provides treatment for several gastrointestinal diseases and disorders. For example, the method may be used in the treatment of dyspepsia, postoperative ileus, irritable bowel syndrome, constipation, diarrhea, fecal incontinence, pain and discomfort associated with visceral organs, obstructed intestines, eating disorders including obesity, nausea and/or emesis, including chemotherapy-induced emesis.

In one version, the method further includes the step of programming a controller in communication with the pulse generator with a stimulation parameter. The controller is located either external and/or internal to the body. The controller can communicate with the pulse generator via any suitable manner such as leads, electromagnetic waves, inductive coupling, or the like. In one preferred embodiment, the controller electromagnetically controls the pulse generator.

Preferably, the controller is programmed with a stimulation parameter either prior to or subsequent to insertion of the stimulation device in the appendix. The stimulation parameter is utilized by the controller to control the stimulation device such that the stimulation device delivers pre-determined types of pulses to the submucosa of the appendix. Stimulation parameters can include frequency, pulse width, amplitude, and the like. It should be understood that the stimulation parameters utilized to control the controller can be modified according to the desires of the designer and/or the user.

In one version, the stimulation device is further provided with a sensor system for detecting environmental conditions around the stimulation device or any part of the gastrointestinal tract. The environmental conditions can be used to determine parameters regarding the external environment of the stimulation device when inserted in the appendix. Information received from the sensor system can provide feedback to help control the stimulation device. The sensor system can include one or more sensors for sensing a variety of different types of environmental factors which may be surrounding the stimulation device or the gastrointestinal tract such as, for example, mechanical contractions, pressure, tension, electrical signals, temperature, pH or the like.

In another version, the stimulation device is further provided with a power source for supplying power to the stimulation device. The power source can be implemented in a variety of manners, such as a battery supported by the stimulation device, or a separate device provided external to the user which provides power to the stimulation device through a wireless mechanism, such as inductive loop coupling.

In another aspect, the present invention is directed to a method of using a stimulation device to emit a medium to the rectum for treatment of a gastrointestinal disorder and/or eating disorder. In general, the stimulation device is inserted into the internal wall of the rectum. The medium is delivered, via the stimulation device, to the rectum for the treatment of the gastrointestinal disorder and/or eating disorder.

In another aspect, the present invention is directed to a stimulator device for emitting a medium to the gastrointestinal tract of a user. In general, the stimulator device is comprised of at least two electrodes sized and shaped for insertion into the mucosa, submucosa or serosa of the appendix of the user. The electrodes supply the medium to the appendix. Additionally, a pulse generator, for delivering pulses of the medium to the electrodes, is placed subcutaneously in the user. Additionally, a controller, in communication with the pulse generator, controls the pulses. Preferably, the electrodes, pulse generator, and controller are supported by a housing.

In another aspect, the present invention is directed to a delivery system for providing a stimulator device to the appendix. In general, the delivery system includes an elongated tubular member having a distal end adapted for insertion into an anal orifice. A stimulator device is supported by the elongated tubular member and deployed in the appendicular area. The stimulator device includes a housing constructed of a bio-compatible non-digestible material; a pulse generator disposed in the housing for generating pulses; a controller disposed in communication with the pulse generator for controlling the pulses; and, at least two electrodes supplying a medium containing the pulses generated by the pulse generator to the gastrointestinal tract.

BRIEF DESCRIPTION OF THE SEVERAL VIEWS OF THE DRAWINGS

So that the above recited features and advantages of the present invention can be understood in detail, a more particular description of the invention, briefly summarized above, may be had by reference to the embodiments thereof that are illustrated in the appended drawings. It is to be noted however that the appended drawings illustrate only typical embodiments of the invention and are therefore not to be considered limiting of its scope, for the invention may admit to other equally effective embodiments.

FIG. 1A is a diagrammatic view of lower digestive system including the appendicular region and rectal region.

FIG. 1B is a schematic block diagram view of one embodiment of a stimulator device positioned in the appendicular region in accordance with the present invention.

FIG. 1C is a diagrammatic view of another embodiment of a stimulator device positioned in the appendicular region in accordance with the present invention.

FIG. 1D is a diagrammatic view of another embodiment of a stimulator device positioned in the rectal region in accordance with the present invention.

FIG. 1E is a diagrammatic view of another embodiment of a stimulator device positioned in the rectal region in accordance with the present invention.

DETAILED DESCRIPTION OF THE EMBODIMENTS

Figure 2:
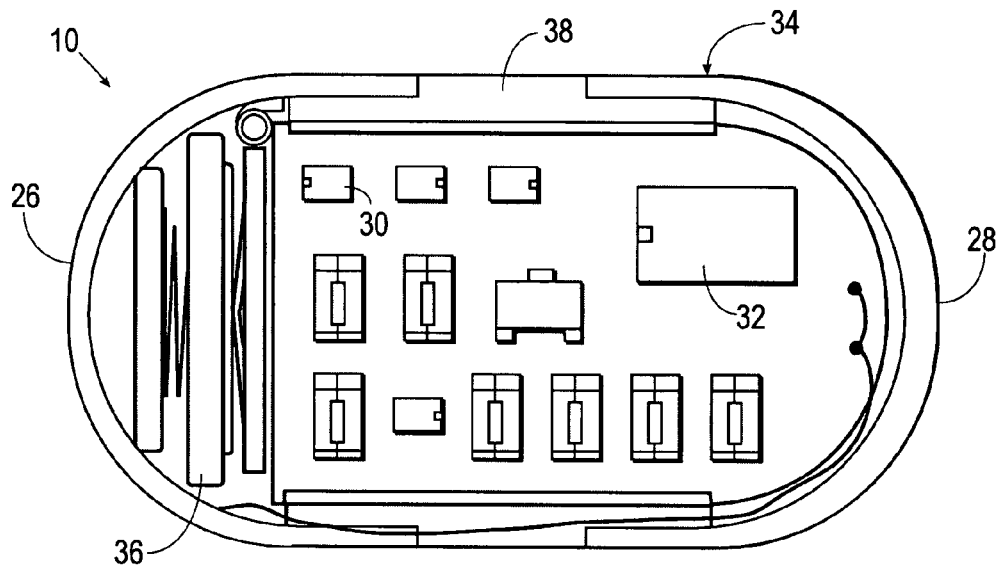
FIG. 2 is a diagrammatic view of the embodiment of the stimulator device illustrated in FIG. 1C and FIG. 1D constructed in accordance with the present invention.

Present embodiments of the invention are shown in the above-identified figures and described in detail below. In describing the embodiments, like or identical reference numerals are used to identify common or similar elements. The figures are not necessarily to scale and certain features in certain views of the figures may be shown exaggerated in scale or in schematic in the interest of clarity and conciseness. Please add/modify explanations of figures based on my addition and changes to the figures.

Referring now to the drawings, and in particular to FIGS. 1A-1E, shown therein and designated by reference numeral 10 is a stimulator device (hereinafter referred to as "stimulator device"), constructed in accordance with the present invention, for providing stimulation to a gastrointestinal tract 12 of a user 14. The gastrointestinal tract 12 of the user 14 includes the alimentary canal and organs associated with the alimentary canal such as the stomach, small intestine, large intestine, and the like. Users 14 may include humans, mammals, or other multicellular organism having a gastrointestinal tract 12.

In general, the stimulator device 10 is placed in the appendix or within an appendicular region 16 and/or rectal region 18 of a lower digestive tract 17 of the user 14. The vermiform appendix is located at the junction of the small intestine and the large intestine. The appendix is generally credited with no significant function and is most commonly explained as a vestigial structure within the body. It is routinely removed without any ill effects or side effects. However, the linkage of the appendix within the ENS to the gastrointestinal tract 12 provides an avenue for electrical stimulation in the treatment of gastrointestinal disorders giving a desirable use and purpose for this vestigial structure.

The rectum is also linked within the ENS to the gastrointestinal tract 12 and offers another option for convenient placement of the stimulator device 10. Specifically, the relative proximity of the anal orifice to the rectum allows placement of the stimulator device 10 in the rectum without the need for extensive surgical procedures currently practiced in gastrointestinal stimulator placement.

Preferably, at least a portion of the stimulator device 10 is placed in contact with the appendicular wall 20 and/or rectal wall 22 of the user 14. The stimulator device 10 may contact the external appendicular wall 20 and/or rectal wall 22, the interior appendicular wall 20 and/or rectal wall 22, and/or be within the appendicular wall 20 and/or rectal wall 22. For example, the stimulator device may be placed in contact with the mucosal surface, underlying vascular submucosa, serosa, and/or layered muscularis externa of the appendicular wall 20 and/or rectal wall 22. Preferably, the stimulator device 10 is inserted into the submucosa of the appendicular wall 20 and/or rectal wall 22.

Optionally, the stimulator device 10 may be attached to the appendicular wall 20 and/or rectal wall 22 to prevent migration of the stimulator device 10 through the gastrointestinal tract 12. The stimulator device 10 may be attached to the appendicular wall 20 and/or rectal wall 22 through the use of projections, barbs, umbrella connectors, sutures, adhesives, and/or the like. Additionally, multiple stimulator devices 10 may be placed within the user 14. For example, the user 14 may have a first stimulator device 10 within the appendicular region 16 and a second stimulator device 10 within the rectal region 18 of the user 14.

Once positioned in contact with the appendicular wall 20 and/or rectal wall 22, the stimulator device 10 delivers pulses of a medium and provides stimulation to the gastrointestinal tract 12 through the enteric nervous system. Placement of the stimulator device 10 within one area of the enteric nervous system provides stimulation not only at the area of contact, but also provides stimulation within other areas of the ENS system. For example, placement of the stimulator device 10 within the appendicular region 16 can provide stimulation initiating peristaltic activity within the gastrointestinal tract 12.

Stimulation of the gastrointestinal tract 12 through the enteric system will alter, inhibit, or excite gastrointestinal motor functions, activate intrinsic and extrinsic neuronal pathways and/or solicit hormonal/peptide releases. The effects of stimulation on these functions/pathways are related to the selection of stimulation parameters which are discussed in greater detail below and have therapeutic potentials for various diseases/disorders. The stimulator device 10 can thus be used for treating a variety of digestive and eating disorders as well as in use in treating chemotherapy-induced emesis. Exemplary eating disorders include obesity, binging, bulimia, and the like. Gastrointestinal disorders include dysphagia, gastroesophageal reflux diseases, functional dyspepsia, gastroparesis, postoperative ileus, irritable bowel syndrome, constipation, diarrhea, fecal incontinence, pain/discomfort, nausea and vomiting, and the like.

The stimulator device 10 can be programmed with stimulation parameters prior to placement of the stimulator device 10 within the appendicular region 16 and/or rectal region 18 of the user 14 so that a particular disease or disorder will be treated. A health care provider or user may be presented with a variety of stimulator devices 10 with each stimulator device 10 pre-programmed to treat a different disorder. Alternatively, the stimulator device 10 can be programmed to treat a particular disorder immediately prior to administration. Alternatively, the stimulator device 10 can be programmed with a variety of different types of treatment regimens for different diseases and/or disorders so that the stimuli can be changed during treatment of the gastrointestinal disorder without need for the removal of the stimulator device 10.

As illustrated in FIGS. 1B and 1E, the stimulator device 10 includes at least two electrodes 26 and 28 in communication with a pulse generator 30. The electrodes 26 and 28 can be provided as one or multiple pairs and in varying shapes. For example, the electrodes 26 and/or 28 can be provided as a point electrode, a ring electrode, or a patch electrode.

The electrodes 26 and 28 may be surgically implanted or insertably placed within the appendicular region 16 and/or rectal region 18. For example, for the placement of stimulator into the appendix or rectum, colonoscopy or endoscopy can be utilitzed. For the placement of stimulator in other areas, various surgical techniques may be used depending on the location of placement. For example, both traditional surgical techniques and/or laparoscopic techniques may be used in placing the stimulator device 10 in the appendicular region 16 and/or rectal region 18. Preferably, laproscopic techniques, using small incisions in comparison to large incisions of traditional surgery, are used to place the stimulator device 10. Additionally, other forms of surgical placement, known now or developed within the future, may be used as long as the stimulation device is placed in contact with the appendicular wall 20 and/or rectal wall 22 of the user 14.

The electrodes 26 and 28 are in communication with the pulse generator 30 such that pulses can be provided from the pulse generator 30 to the electrodes 26 and 28. The pulse generator delivers a frequency of pulses to the electrodes 26 and 28 providing emission of the medium to the appendicular wall 20 and/or rectal wall 22. For example, the pulse generator 30 delivers pulses to the electrodes 26 and 28 in contact with the appendicular wall 20 such that the electrodes 26 and 28 provide stimulation to the gastrointestinal tract 12 of the user 14 through the enteric nervous system.

The pulses provided by the pulse generator 30 to the electrodes 26 and 28 can be provided in a variety of different manners, such as intermittent pulses, continuous pulses, and/or a train of intermittent and/or continuous pulses. Selection of the pulses is determined based on the particular gastrointestinal disease(s) and/or disorder(s) being treated as described in more detail below.

Such pulses can be delivered via the pulse generator 30 to the electrodes 26 and 28 via any suitable medium, such as electricity, acoustic waves, radiation, photons, or the like. Preferably, the medium is in the form of electrical stimulation to the appendicular wall 20 and/or rectal wall 22.

The pulse generator 30 adjacent to the electrodes 26 and 28 or separate from the electrodes 26 and 28. In one embodiment, the pulse generator 30 is separate from the electrodes 26 and 28 and inserted subcutaneously within the abdominal region. Preferably, the pulse generator 30 is inserted subcutaneously within the abdominal region above the belt line of the user 14. In another embodiment, as illustrated in FIG. 1C and 1D, the pulse generator 30 is adjacent to the electrodes 26 and 28.

Additionally, pulse generator 10 may utilize an internal power source or an external power source. It is contemplated that the power source may be located external to the user 14, provided the power source is in communication with the pulse generator 30. For example, the power source may be provided external to the user 14 through a wireless mechanism, such as inductive loop coupling, electromagnetic control, or the like.

The stimulator device may optionally include a controller 32. The controller 32 communicates with the pulse generator 30 for controlling the pulses generated by the pulse generator 30. The controller 32 can be analog, digital, or a combination of both. The controller 32 may be a computer, a microcontroller, a microprocessor, or the like.

The controller 32 uses stimulation parameters to regulate the pulse generator 30 and provide a variety of different types of treatment regimens for different diseases and/or disorders. Stimulation parameters, as discussed in more detail below, may include frequency, pulse width, amplitude, and the like. Programming of the controller 32 can regulate pulses generated by the pulse generator 30 so that can the pulses change based upon the treatment regime for the user 14. The controller 32 may be programmed with stimulation parameters prior to insertion and/or placement of the stimulator device 10 and/or after insertion and/or placement of the stimulator device 10.

Shown in FIG. 2 is a diagrammatic view of one example of the stimulator device illustrated in FIG. 1C and FIG. 1D constructed in accordance with the present invention. The stimulator device 10 is provided with two electrodes 26 and 28, the pulse generator 30, and the controller 32. Additionally, the stimulator device includes a housing 34 and a power source 36.

The housing 34 is constructed of a biocompatible, non-digestible material for use within the appendicular region 16 and/or the rectal region 18 of the user 14. Examples of biocompatible, non-digestible materials suitable for use in forming the housing 34 are, but not limited to, biocompatible metals, such as unalloyed titanium, wrought titanium alloy, nitrogen austenitic steel, stainless steel, and biocompatible plastic such as polyvinylchloride, polytetrafluoroethelyne, polyethersulfone, polyurethane, polycarbonate, polyeretherketone and polypropylene.

The housing 34 is sized and shaped for placement within the appendicular region 16 and/or rectal region 18. Preferably, the housing is sized and shaped for transport through the anal orifice. For example, the housing 34 can be shaped in the form of a capsule. However, it should be understood that the housing 34 can be provided in other shapes and/or sizes, so long as the housing 34 can be inserted through the anal orifice and/or placed in at least a portion of the appendicular region 16 and/or rectal region 18 preferably without causing any negative side effects, such as irritation. It is also desirable for the housing 34 to be sized and shaped so as not to block the appendicular region 16 and/or rectal region 18 leading to interference with the operation of the gastrointestinal tract 12. Further, it should be understood that rather than simply being constructed of a biocompatible, non-digestible material, the housing 34 can be formed of a non-biocompatible, or even digestible material that is coated with a biocompatible non-digestible material.

The housing 34 is formed with the electrodes 26 and 28 separated by an insulating material 38. The electrodes 26 and 28 are connected to the insulating material 38 so as to form a sealed container. The housing 34 defines an interior space containing the pulse generator 30, the controller 32, and the power source 36. However, it should be understood that at least the power source 36, and the controller 32 can be external to the housing 34 so long as the power source 36 and/or controller 32 can communicate and/or provide power, and/or control to the pulse generator 30.

As discussed above, the controller 32 communicates with the pulse generator 30 for controlling the pulses generated by the pulse generator 30. The electrodes 26 and 28 supply a medium containing the pulses generated by the pulse generator 30 to the appendicular wall 20 and/or rectal wall 22. As discussed above, the medium can be provided in a variety of forms such as electricity, acoustic waves, radiation, photons, or the like.

The electrodes 26 and 28 can be provided as one or multiple pairs and can be provided on the housing 34 in various locations and different shapes. For example, the electrodes 26 and/or 28 can be provided as a point electrode, a ring electrode, or a patch electrode. The distance between the electrodes 26 and 28 in a pair can also vary.

As shown in FIG. 2, the controller 32 is supported by the housing 34 and is contained within the interior space of the housing 34. The controller 32 can be external to the housing 34 or at least portions of the controller 32 can be external to the housing 34 so long as the controller 32 can communicate with and/or control the pulse generator 30.

The power source 36 is also supported by the housing 34. Preferably, the power source 36 is within the internal space of the housing 34. However, it is contemplated that the power source 36 may be located external to the housing 34, provided the power source 36 is in communication with the pulse generator 30 and/or the controller 32. For example, the power source 36 may be provided external to the user 14 through a wireless mechanism, such as inductive loop coupling, electromagnetic control, or the like.

The housing 34 may optionally include means for attaching the stimulator device 10 to the appendicular wall 20 and/or rectal wall 22. As previously discussed, attachment means include, but are not limited to, projections, barbs, umbrella connectors, sutures, adhesives, and/or the like.

Figure 3:
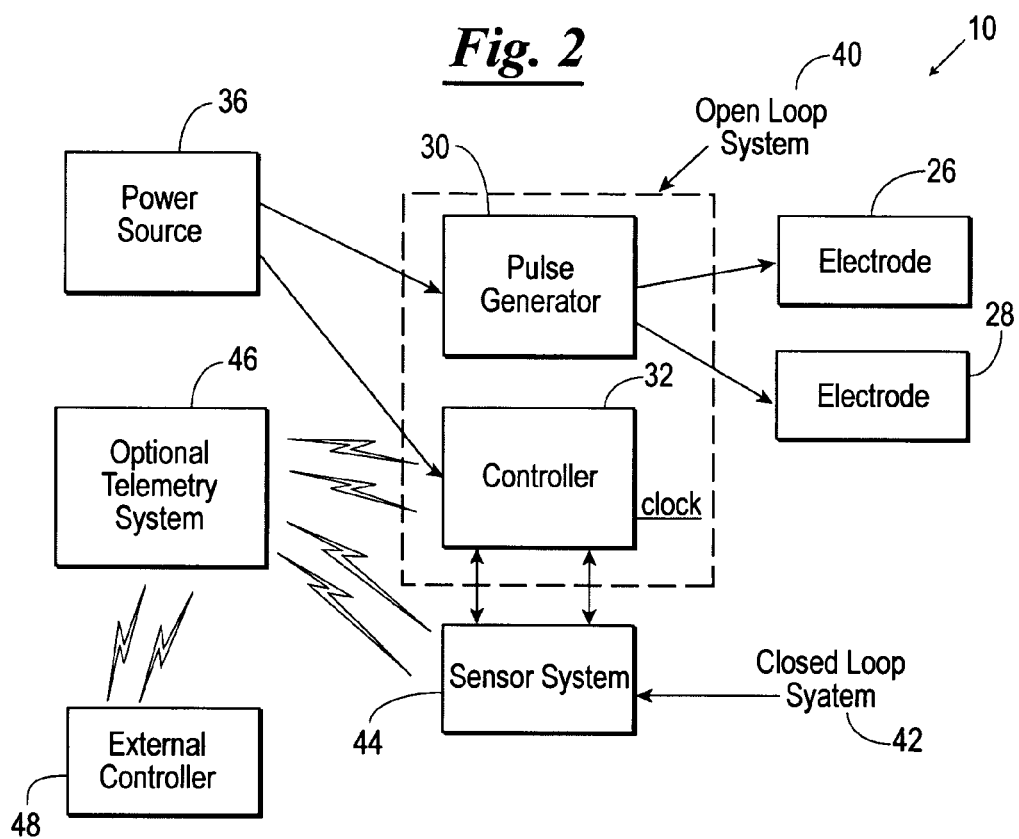
FIG. 3 is a schematic, block diagram of another embodiment of a stimulator device constructed in accordance with the present invention.

Referring to FIG. 3, regulation of the pulse generator 30 by the controller 32 may include an open-loop system 40, a closed loop system 42, or a combination of the like. In the open loop system 40, pulses are delivered to the electrodes 26 and 28 without the use of sensing inputs such as a sensor system 44. In the closed loop system 42, pulses are delivered to the electrodes 26 and 28 based on inputs to the controller 32 via the sensor system 44. For example, the sensor system 44 can deliver electrical signals to the controller 32 that vary or are indicative of the following conditions: mechanical contractions, pressure, tension, electrical signals, temperature, pH or the like. Although FIG. 3 shows the controller 32, it should be noted the stimulator device 10 may include the pulse generator 30 supplying pulses to the electrodes 26 and 28 without the use of the controller 32.

One embodiment of the open loop system 40 includes the controller 32, the pulse generator 30, and the electrodes 26 and 28. The controller 32 is in communication with the pulse generator 30 and regulates pulses generated by the pulse generator 30. The pulse generator 30 provides the pulses to the electrodes 26 and 28. The controller 32 may optionally contain a timing mechanism, such as an internal clock, for further controlling the pulses. In another embodiment (not illustrated), the controller 32 is in direct communication with the electrodes 26 and 28 directly and alters the pulses supplied to the electrodes 26 and 28 directly.

The closed-loop system 42, as illustrated in FIG. 3, includes the controller 32, the pulse generator 30, the electrodes 26 and 28, and the sensor system 44. The sensor system 44 communicates with the controller 32 and detects environmental conditions external to the stimulator device 10. The environmental conditions can be used to determine the location of the stimulator device 10 within the gastrointestinal tract 12 of the user 14 if the stimulator device 10 migrates. Additionally the environmental conditions can be used to vary the frequency and/or intensity of the pulses generated by the pulse generator 30 as needed. The sensor system 44 can include one or more sensors for sensing a variety of different types of environmental factors which may be surrounding the stimulator device 10. For example, mechanical contractions, pressure, tension, electrical signals, temperature, pH or the like.

The information received from the sensor system 44 is fed back to the controller 32 so that the controller 32 can vary stimulation parameters and regulate pulses generated by the pulse generator 30. For example, the sensor system 44 can detect the effect of stimulation to the appendicular region 16 and/or rectal region 18. The location or effect of the stimulator device 12 within the user 14 is fed back to the controller 32. The controller 32 then regulates the frequency, duration, and/or amplitude of the pulses generated by the pulse generator 30 based on the effect of the stimulator device 10 within the appendicular region 16 and/or rectal region 18 of the user 14.

The sensor system 44 can also provide a method for synchronized stimulation such that pulses can be provided to the appendicular region 16 and/or rectal region 18 of the user 14 upon detection by the sensor system 44 of a mechanical contraction within the user 14. Synchronizing each pulse with the intrinsic physiological activity of the user 14 may enhance gastrointestinal contractions and accelerate transport of nutrients along the gastrointestinal tract.

As illustrated in FIG. 3, the stimulator device 10 may optionally include a telemetry system 46 that assists in providing external control, external programming, and/or permitting measurement and reporting of information regarding the stimulator device 10 and/or the environmental conditions surrounding the stimulator device 10. The telemetry system provides communication between an internal controller, located within the user 14 such as the sensor system 44 and/or controller 32, while an external controller 48 is external to user. The external controller 48 can be either proximally located to the user 14 or located at a distance to the user 14 so long as the telemetry system can provide communication between the internal controller, such as the sensor system 44 and/or controller 32, and the external controller 48. The communication can be through radio frequency, infrared light, laser light, visible light, acoustic energy, or the like. Both the internal controller, such as the sensor system 44 and/or controller 32, and external controller 48 are preprogrammed to provide monitoring, alerting, transmitting, and/or record-keeping of information generated and/or needed for the stimulator device 10.

In one embodiment, communication between the sensor system 44, as the internal controller, and a microprocessor, as the external controller 48, provides monitoring of environmental information surrounding the stimulator device 10 and provides an alerting function if the microprocessor and/or sensor system 44 detect abnormal conditions within the appendicular region 16 and/or rectal region 18 of the user 14. In another embodiment, communication between the sensor system 44, as the internal controller, and the microprocessor, as the external controller 48, allows for the analysis of the environmental information using a decision-making algorithm to provide stimulation parameters. The environmental information is provided by the sensor system 44 and communicated by the telemetry system 46 to the microprocessor. The microprocessor uses the algorithm to determine the stimulation parameters. Such stimulation parameters are communicated again through the telemetry system 46 to either the controller 32 and/or sensor system 44 to regulate the pulses generated by the pulse generator 30.

As previously discussed, stimulation parameters are utilized by the controller 32 to control the pulse generator 30. Stimulation parameters can include frequency, pulse width, amplitude, and the like. The pulses may be intermittent pulses, continuous pulses, and/or trains of intermittent and/or continuous pulses. The controller 32 can vary the stimulation parameters to provide variations in the pulses such that the pulse generator 32 provides long-pulse, short-pulse, dual phase pulses, trains of short-pulses, biphasic trains of pulses, or other variation of pulses. FIGS. 4a-e graphically illustrates the relative duration and amplitude of a variety of the exemplary pulses which can be generated by a pulse generator 30 based on the various stimulation parameters provided by the controller 32. It should be understood that the stimulation parameters utilized by the controller 32 can be modified according to the desires of the designer and/or the patient.

Figure 4:
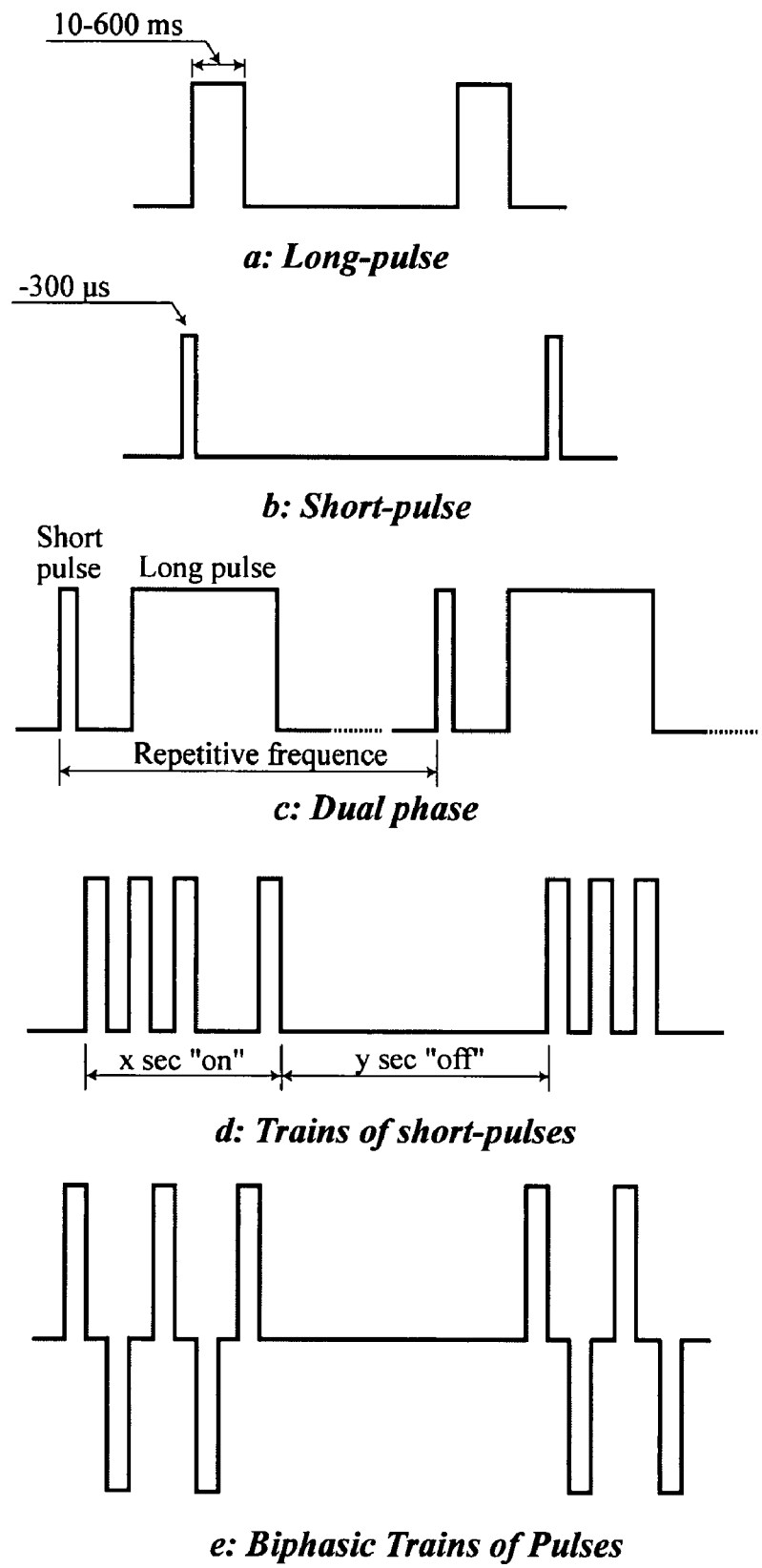
FIGS. 4a-4e illustrate a variety of exemplary pulses which can be generated by a stimulator devices for treating a variety of types of gastrointestinal disorders.

FIG. 4a graphically illustrates repetitive long-pulses having a pulse width in the order of milliseconds. The long pulse method is able to 'pace' or entrain natural slow waves of the digestive tract. In this method, the electrical stimulus is composed of repetitive single pulses with a pulse width in the order of milliseconds and a stimulation frequency in the vicinity of the physiological frequency of the gastric slow wave as detailed in the article "Systematic review: applications and future of gastric electrical stimulation" by J. Zhang and J. D. Z. Chen in *Alimentary Pharmacology & Therapeutics*, Volume 24, pages 991-1002 (2006) that is hereby incorporated by reference in its entirety.

FIG. 4b graphically illustrates repetitive short pulses having a pulse width that is substantially shorter than the long pulse of FIG. 4a and is in the order of a few hundred microseconds as opposed to milliseconds. The stimulation frequency is usually a few times higher or substantially higher than the physiological frequency of the gastric slow wave.

FIG. 4c graphically illustrates the combining of short pulses and long pulses into a dual phase pulsing. This repetitive pulsing method is composed of one short pulse, or a multitude of short pulses, in the order of a few hundred microseconds, followed by a long pulse, in the order of a few hundred millisecond. Dual phase pulsing has been shown to provide normalizing of gastric dysrhythmia and improvement in the symptoms such as nausea and vomiting. Alternatively, dual phase pulsing may include a long pulse followed by a short pulse, or other combinations of long and short pulses.

FIG. 4d graphically illustrates repetitive trains of pulses derived from the combination of two signals. The first signal is a continuous short pulse with a high frequency. The second signal is a control signal to turn the pulses on and off. For example, the second signal can contain a stimulation parameter providing that the duration of the pulse is 'on' for x seconds and 'off' for y seconds. The addition of x and y can then determine the frequency of the pulse train. This kind of stimulation is frequently used in nerve stimulation and other related areas. It should be understood that trains of pulses can include trains of short-pulses, trains of long-pulses, and/or a combination of the both long and short pulses.

FIG. 4e graphically illustrates biphasic trains of pulses in which pulse pairs are repeatedly symmetrically generated. The first pulse of each pair has a positive amplitude and the second pulse of each pair has a negative amplitude. Similar to FIG. 4d, pulses are repeatedly generated from the combination of two signals. The first signal includes continuous pulse pairs that are repeatedly symmetrically generated. The second signal is a control signal to turn the pulses on and off. For example, the second signal can contain a stimulation parameter providing that the duration of the pulse is 'on' for x seconds and 'off' for y seconds. The addition of x and y can then determine the frequency of the pulse train.

It is contemplated, that in certain applications, it may be beneficial to vary the pulses during treatment of the gastrointestinal disorder or in the treatment of multiple disorders. For example, short pulses may be used if the device is used for treating disorders associated with the nervous systems such as pain, nausea and vomiting, long pulses or train of pulses may be used if the device is used for treating disorders associated with the movement of nutrient through the gastrointestinal tract, such as obesity or impaired gastrointestinal motility; a combination of short and long pulses will be used if the device is used to treat disorders affected by both the nervous systems and gastrointestinal motility. Additionally, although a particular pulse may be used by stimulator device 10, it may be beneficial to vary the amplitude, frequency, and/or duration of the pulse depending on location of the stimulator device 10.

As discussed above, the stimulator device 10 is used to emit a medium for treatment of eating disorders such as obesity or a gastrointestinal disorder or disease, such as dysphagia, gastroesophageal reflux diseases, functional dyspepsia, gastroparesis, postoperative ileus, irritable bowel syndrome, constipation, diarrhea, fecal incontinence, pain/discomfort, nausea and vomiting, obesity, eating disorders as well as in the treatment of chemotherapy-induced emesis.

In general, use of the stimulator device 10 includes providing the stimulator device 10 to the user 14. The stimulator device 10 is placed in the gastrointestinal tract 12 of the user 14. Methods of administering the stimulator device 10 include placement of the stimulator device within the appendicular region 16 and/or rectal region 18 of the user 14 such as through traditional surgical procedures, laparoscopic procedures, and the like.

Additionally, methods of administering the stimulator device 10 may include non-surgical methods such as insertion of the stimulator device 10 into the anal orifice of the user through the use of a delivery catheter. The delivery catheter includes an elongated tubular member having at least one end adapted for insertion into the anal orifice. The stimulator device 10 is supported by the elongated tubular member for deployment within the appendicular region 16 and/or rectal region 18.

Once the stimulator device 10 is in contact with the appendicular wall 20 and/or rectal wall 22, the stimulator device 10 delivers pulses of the medium for treatment of gastrointestinal diseases and/or disorders. Such pulses can be intermittent pulses, continuous pulses, and/or trains of intermittent and/or continuous pulses as discussed previously.

It is contemplated that the stimulator device 10 may be distributed in a variety of methods. One method of distribution may include providing the stimulator device 10 to the user 14 by a medical professional. For example, a pharmaceutical distributor can distribute the stimulator device 10 to a medical professional for use in treating gastrointestinal disorders, diseases, and/or for use in chemotherapy-induced emesis. Alternatively, the stimulator device 10 can be distributed to a pharmacy and/or provided to a retailer for over-the-counter distribution to a user 14 for use in treating gastrointestinal disorders, diseases and/or for use in chemotherapy-induced emesis as well as obesity. The pharmacy and/or retailer may then sell the stimulator device 10 directly to the user 14. Additionally, the stimulator device 10 may be provided in a kit containing the delivery catheter.

The foregoing disclosure includes the best mode for practicing the invention. It is apparent, however, that those skilled in the relevant art will recognize variations of the invention that are not described herein. While the invention is defined by the appended claims, the invention is not limited to the literal meaning of the claims, but also includes these variations.

What is claimed:

1. A method of treating of a gastrointestinal disorder, comprising the steps of:
    placing a stimulation device in contact with an appendicular wall of a user, the stimulation device having at least two electrodes in communication with a pulse generator;
    delivering, via the pulse generator, pulses to the electrodes; and,
    emitting, by the electrodes, a medium to the appendicular wall;
    wherein the medium delivered to the appendicular wall provides enteric nervous system stimulation for treatment of the gastrointestinal disorder.

2. The method of claim 1, wherein the stimulation device is endoscopically inserted into the luminal cavity of the appendix.

3. The method of claim 1, wherein the stimulation device is placed using surgical techniques.

4. The method of claim 1, wherein the gastrointestinal disorder is dyspepsia.

5. The method of claim 1, wherein the gastrointestinal disorder is postoperative ileus.

6. The method of claim 1, wherein the gastrointestinal disorder is irritable bowel syndrome.

7. The method of claim 1, wherein the gastrointestinal disorder is constipation.

8. The method of claim 1, wherein the gastrointestinal disorder is diarrhea.

9. The method of claim 1, wherein the gastrointestinal disorder is fecal incontinence.

10. The method of claim 1, wherein the gastrointestinal disorder is pain and discomfort associated with visceral organs.

11. The method of claim 1, wherein the gastrointestinal disorder is an obstructed gastrointestinal tract.

12. The method of claim 1, wherein the gastrointestinal disorder is an eating disorder.

13. The method of claim 12, wherein the eating disorder is obesity.

14. The method of claim 12, wherein the eating disorder is bulimia.

15. The method of claim 12, wherein the eating disorder is anorexia.

16. The method of claim 12, wherein the eating disorder is binge eating.

17. The method of claim 1, wherein the gastrointestinal disorder is nausea.

18. The method of claim 17, wherein the nausea is chemotherapy-induced.

19. The method of claim 1, wherein the gastrointestinal disorder is emesis.

20. The method of claim 19, wherein the emesis is chemotherapy-induced.

21. The method of claim 1, further comprising the step of programming a controller in communication with the stimulation device with a stimulation parameter.

22. The method of claim 21, wherein the controller is programmed prior to placement of the stimulation device in contact with the appendicular wall.

23. The method of claim 1, wherein the stimulation device delivers continuous pulses of the medium.

24. The method of claim 1, wherein the stimulation device delivers intermittent pulses of the medium.

25. The method of claim 1, wherein the stimulation device delivers a train of pulses of the medium.

26. The method of claim 1, wherein the electrodes are sized and shaped to be inserted into the appendix.

27. The method of claim 26, further comprising the step of inserting a pulse generator subcutaneously within the abdominal region, wherein the pulse generator delivers a frequency of pulses to the electrodes.

28. The method of claim 27, further comprising the step of controlling, by a controller, the pulse generator.

* * * * *